(12) United States Patent
Lee et al.

(10) Patent No.: US 12,357,685 B2
(45) Date of Patent: Jul. 15, 2025

(54) VACCINE COMPOSITION FOR PREVENTING RABIES, AND PREPARATION METHOD THEREOF

(71) Applicants: BIOAPPLICATIONS INC., Gyeongsangbuk-do (KR); REPUBLIC OF KOREA(ANIMAL AND PLANT QUARANTINE AGENCY), Gyeongsangbuk-do (KR)

(72) Inventors: Yong Jik Lee, Gyeongsangbuk-do (KR); Sangmin Lee, Gyeongsangbuk-do (KR); Jae-Young Song, Gyeonggi-do (KR); In-Ohk Ouh, Gyeongsangbuk-do (KR); Soo Dong Cho, Gyeonggi-do (KR); Seyeon Park, Gyeongsangbuk-do (KR); Beong Sul Kang, Gyeongsangnam-do (KR); Dong-Kun Yang, Gyeonggi-do (KR); Ha-Hyun Kim, Gyeongsangbuk-do (KR)

(73) Assignees: BIOAPPLICATIONS INC., Gyeongsangbuk-do (KR); REPUBLIC OF KOREA(ANIMAL AND PLANT QUARANTINE AGENCY), Gyeongsangbuk-do (KR)

( * ) Notice: Subject to any disclaimer, the term of this patent is extended or adjusted under 35 U.S.C. 154(b) by 877 days.

(21) Appl. No.: 17/333,052

(22) Filed: May 28, 2021

(65) Prior Publication Data

US 2021/0283241 A1    Sep. 16, 2021

Related U.S. Application Data

(63) Continuation-in-part of application No. PCT/KR2019/016569, filed on Nov. 28, 2019.

(51) Int. Cl.
A61K 48/00 (2006.01)
A23K 10/16 (2016.01)
(Continued)

(52) U.S. Cl.
CPC ............ *A61K 39/205* (2013.01); *A23K 10/16* (2016.05); *A61P 31/14* (2018.01); *C07K 1/14* (2013.01)

(58) Field of Classification Search
None
See application file for complete search history.

(56) References Cited

U.S. PATENT DOCUMENTS 5,856,178 A * 1/1999 White .............. C07K 14/43563
435/375
2009/0004215 A1   1/2009 Tuli et al.

FOREIGN PATENT DOCUMENTS

CA    3040337 A1    5/2018
CN    103998601 A   8/2014
(Continued)

OTHER PUBLICATIONS

Hyun et al., "Molecular epidemiology of rabies virus isolates from South Korea," Virus Research 114: 113-125 (Year: 2005).*
WIPO English translation of WO2018135860 (Year: 2018).*
Chinese Office Action for App. No. CN201980077602.8, Dated Apr. 28, 2023, 12 Pages.
(Continued)

*Primary Examiner* — M Franco G Salvoza
(74) *Attorney, Agent, or Firm* — Riverside Law LLP

(57) ABSTRACT

The present invention relates to: a rabies virus glycoprotein comprising an amino acid sequence represented by SEQ ID NO: 2; a recombinant vector for producing the glycoprotein; a transformant comprising the vector; and a vaccine composition comprising the rabies glycoprotein, and the like.

6 Claims, 4 Drawing Sheets

Specification includes a Sequence Listing.

```
┌─────────┬──────────────────────┬──────────────┐
│  BiP    │         RVGe         │  6His  HDEL  │
└─────────┴──────────────────────┴──────────────┘
```

(51) Int. Cl.
    *A61K 39/205*    (2006.01)
    *A61P 31/14*     (2006.01)
    *C07K 1/14*      (2006.01)

(56)           References Cited

FOREIGN PATENT DOCUMENTS

| KR | 10-2013-0111581 A     |   | 10/2013 |              |
|----|-----------------------|---|---------|--------------|
| KR | 10-2018-0084680 A     |   | 7/2018  |              |
| KR | 2020059962 A1         |   | 3/2020  |              |
| WO | WO-2009105357 A1      | * | 8/2009  | ......... C07K 14/4725 |
| WO | WO-2018104919 A1      | * | 6/2018  | ............. A61K 39/12 |
| WO | WO-2018135860 A1      | * | 7/2018  | ............. A61K 38/17 |

OTHER PUBLICATIONS

Li Y, et al., "Latest Advances in Modern Biotechnology," Jilin University Press, Apr. 2013, 9 Pages.

Xu Y Q, "Study on Rabies Virus Glycoprotein DNA Vaccine," Master's Thesis, Jilin University, Oct. 15, 2017, 16 Pages.

Extended European Search Report for App. No. EP19890724.8, Dated Aug. 29, 2022, 7 Pages.

Yang, D.-K., et al., "Molecular characterization of Korean rabies virus isolates", J. Vet. Sci., 2011, 12(1): 57-63.

Oem, J.-K., et al., "Reemergence of Rabies in the Southern Han River Region, Korea", Journal of Wildlife Diseases, 2014, 50(3): 681-688.

Astray, R. M., et al., "Rabies vaccine development by expression of recombinant viral glycoprotein", Arch Virol, 2017, 162: 323-332.

* cited by examiner

FIG.1

| BiP | RVGe | 6His | HDEL |

| serum | | pre | post | pre | post |
|---|---|---|---|---|---|
| CT | 1 | 0.049 | 0.053 | | |
| | 2 | 0.053 | 0.062 | | |
| | 3 | 0.047 | 0.051 | | |
| | 4 | 0.050 | 0.064 | | |
| RVGe | 1 | 0.047 | 4.310 | | |
| | 2 | 0.053 | 3.421 | | |
| | 3 | 0.048 | 4.325 | | |
| | 4 | 0.047 | 4.541 | | |
| | 5 | 0.045 | 4.310 | | |

VACCINE COMPOSITION FOR PREVENTING RABIES, AND PREPARATION METHOD THEREOF

CROSS-REFERENCE TO RELATED APPLICATIONS

This application is a continuation-in-part of International Patent Application No. PCT/KR2019/016569, filed Nov. 28, 2019, which claims the benefit of priority from Korean Patent Application No. 10-2018-0150436, filed on Nov. 29, 2018, the contents of each of which are incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206132-0117-00US Sequence Listing.txt" in ASCII format. The text file containing the Sequence Listing of the present application was created on May 26, 2021 and is 7,177 bytes in size.

TECHNICAL FIELD

The present invention relates to a rabies virus glycoprotein comprising an amino acid sequence represented by SEQ ID NO: 2 and a vaccine composition for preventing rabies, including the glycoprotein as an active ingredient.

BACKGROUND ART

As rabies is a disease that occurs when animals carrying the rabies virus bite people, many people are exposed to the rabies virus because not only various animals living in the wild but also pets carry the rabies virus, and 70.000 or more people are reported to die from rabies every year. Recently, the incidence of rabies caused by pets has decreased sharply by regularly vaccinating pets, but forest-type propagation generated by wild animals such as raccoons and badgers is still maintained.

Meanwhile, vaccines for preventing such rabies are being produced using mainly animal cells without using bacteria due to problems such as protein folding and glycosylation. However, for a vaccine production method using animal cells, the vaccine is not easy to be produced because it costs a lot to expand the equipment for mass production, and in most cases, the vaccine price is high. Further, inactivated rabies virus vaccines prepared using animal cells have disadvantages of not only being difficult to store, but also being highly likely to be contaminated with viruses that can infect animals. However, unlike animal cells, plants are extremely unlikely to be contaminated with viruses that can infect animals, and a vaccine can be mass-produced at any time as long as a cultivation area is secured and can be stored for a long period of time through a plant body, so that it is expected that an inexpensive vaccine can be stably produced (Korean Patent Application Laid-Open No. 10-2013-0111581).

DISCLOSURE

Technical Problem

The present invention has been derived in order to solve the problems in the related art as described above, and an object thereof is to provide a recombinant rabies virus glycoprotein that can be efficiently produced using a plant body and shows high immunogenicity and virus neutralizing ability, a vaccine composition including the same, a method for preparing the glycoprotein, and the like.

However, the technical problems which the present invention intends to solve are not limited to the technical problems which have been mentioned above, and other technical problems which have not been mentioned will be clearly understood by a person with ordinary skill in the art to which the present invention pertains from the following description.

Technical Solution

The present invention provides a rabies virus glycoprotein comprising an amino acid sequence represented by SEQ ID NO: 2. The rabies virus glycoprotein also includes functional equivalents of the amino acid sequence represented by SEQ ID NO: 2 within the scope of the present invention, the functional equivalent has, as a result of addition, substitution, or deletion of an amino acid, a sequence homology of at least 60% or more, preferably 70% or more, more preferably 80% or more, and most preferably 90% or more with the amino acid sequence, and refers to a polypeptide showing substantially the same activity as that of the amino acid sequence represented by SEQ ID NO: 2, and is not limited thereto as long as the amino acid sequence is an amino acid sequence of a rabies virus glycoprotein which can be stably produced using a plant body.

In addition, the present invention provides a vaccine composition for preventing rabies and a feed composition for preventing rabies, comprising the rabies virus glycoprotein as an active ingredient.

Furthermore, the present invention provides a method for preventing or treating rabies by administering the rabies virus glycoprotein to an individual.

Further, the present invention provides a use of the rabies virus glycoprotein for preventing or treating rabies.

In addition, the present invention provides a vector for expressing a rabies virus glycoprotein, comprising a polynucleotide encoding an amino acid sequence represented by SEQ ID NO: 2. The polynucleotide is preferably a polynucleotide sequence represented by SEQ ID NO: 1.

In an exemplary embodiment of the present invention, the vector may be sequentially linked so as to be operable in a sequence of a promoter gene and a polynucleotide encoding an amino acid sequence represented by SEQ ID NO: 2.

In another exemplary embodiment of the present invention, the promoter is a cauliflower mosaic virus-derived 35S promoter, a cauliflower mosaic virus-derived 19S RNA promoter, an actin protein promoter of a plant, a ubiquitin protein promoter, a cytomegalovirus (CMV) promoter, a simian virus 40 (SV40) promoter, a respiratory syncytial virus (RSV) promoter, an elongation factor-1 alpha (EF-1α) promoter, an Emu promoter, a Mannopine synthase (MAS) promoter, a histone promoter, a Clp promoter, and the like, but is not limited thereto.

In still another exemplary embodiment of the present invention, the recombinant expression vector may further include a polynucleotide encoding a chaperone binding protein (BiP), a gene encoding a His-Asp-Glu-Leu (HDEL) peptide, a gene encoding four or more consecutive histidines, and the like.

Furthermore, the present invention provides a transgenic organism transformed with the vector.

In an exemplary embodiment of the present invention, the transgenic organisms may be microorganisms such as *Escherichia coli, Bacillus, Salmonella*, and yeast, animal cells including insect cells and human cells, animals such as a mouse, a rat, a dog, a monkey, a pig, a horse, and a cow, *Agrobacterium tumefaciens*, a plant, and the like, the plant may be food crops including rice, wheat, barley, corn, soybean, potato, wheat, red bean, oats, and sorghum; vegetable crops including thale-cress, Chinese cabbage, white radish, peppers, strawberry, tomatoes, watermelon, cucumber, cabbage, oriental melon, pumpkin, spring onion, onion, and carrot; specialty crops including ginseng, tobacco, cotton, sesame, sugarcane, sugar beet, perilla, peanut, and rapeseed; fruits including apples, pears, jujubes, peaches, grapes, tangerines, persimmons, plums, apricots, and bananas; flowering plants including roses, carnations, chrysanthemums, lilies, and tulips, and the like, but is not limited thereto as long as it may be an organism which may be transformed with the vector of the present invention.

Further, the present invention provides a method for producing a rabies virus glycoprotein, the method including: (a) culturing the transgenic organism; and (b) isolating a rabies virus glycoprotein from the transgenic organism or culture solution and purifying the isolated rabies virus glycoprotein. The transgenic organism may be preferably a cell itself, a plant body, or a culture product including the cell, and the culture solution may be preferably a culture solution from which cells are removed after the cells are cultured, but is not limited thereto as long as it includes a recombinant rabies virus glycoprotein of the present invention.

Advantageous Effect

Since the rabies virus glycoprotein according to the present invention is not only effectively expressed in a plant body, but also has high solubility and thus is easy to isolate and purify, a rabies virus glycoprotein can be mass-produced at low cost, so that it is expected that the rabies virus glycoprotein according to the present invention can be widely used in various fields in which a rabies virus glycoprotein is used. Further, the rabies virus glycoprotein according to the present invention can also be used as a novel rabies vaccine composition because it exhibits remarkable immunogenicity and virus neutralizing ability in the body.

DESCRIPTION OF DRAWINGS

FIG. 1 is a view illustrating the arrangement of genes for expressing a recombinant rabies virus glycoprotein according to an exemplary embodiment of the present invention.

FIG. 2 is a view illustrating the results of confirming the solubility of a recombinant rabies virus glycoprotein according to an embodiment of the present invention by western blotting.

FIG. 5 is a view illustrating the results of confirming the immunogenicity of a recombinant rabies virus according to an exemplary embodiment of the present invention.

MODES OF THE INVENTION

Figure 3:
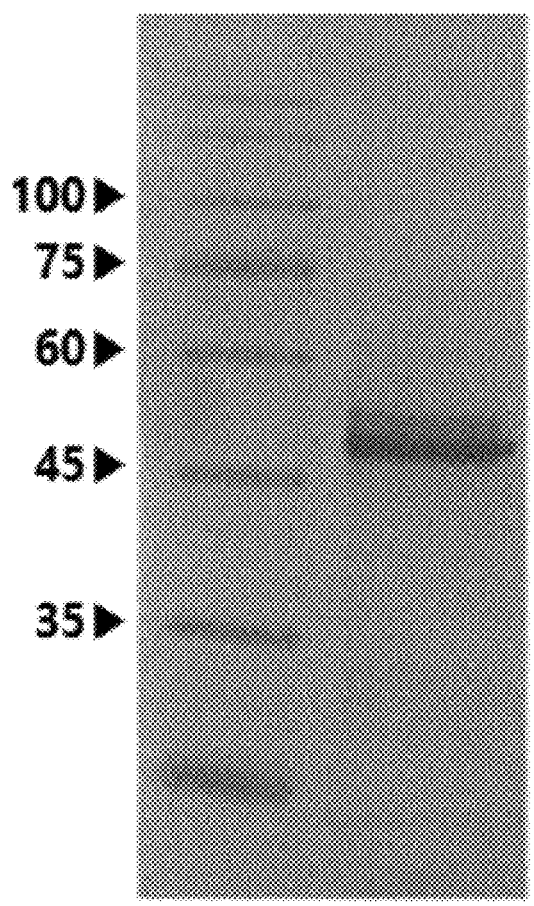
FIG. 3 is a view illustrating the results confirmed by SDS-PAGE after isolating a recombinant rabies virus glycoprotein according to an exemplary embodiment of the present invention and purifying the isolated recombinant rabies virus glycoprotein.

In the present invention, it was confirmed that when a rabies virus glycoprotein gene represented by SEQ ID NO: 1 was used, a rabies virus glycoprotein having high immunogenicity and virus neutralizing ability could be efficiently produced and isolated even in a plant body. Therefore, since the rabies virus glycoprotein of the present invention can be stably and efficiently mass-produced, it is expected that an inexpensive and stable rabies vaccine can be provided.

As used herein, the "antigen" generally refers to all materials that cause an immune response in the body, and is preferably a virus, a chemical, a bacterium, pollen, a cancer cell, shrimp, and the like or a partial peptide or protein thereof, but is not limited thereto as long as it is a material that may cause an immune response in the body.

As used herein, "rabies virus" refers to the most well-known pathogen of Rhabdoviridae and belongs to the genus Lyssavirus, the genome of Rhabdoviridae consists of a non-segmented negative single-stranded RNA of about 11 to 15 kb, and five genes are arranged in the order of 3'-N (nucleoprotein)-P (phosphoprotein)-M (matrix protein)-G (glycoprotein)-L (polymerase)-5'. The rabies virus has a bullet-shaped outer capsid, and the outer capsid portion consists of a bilayer lipid membrane containing a glycoprotein (G) and a matrix protein (M). The glycoprotein is preferably represented by an amino acid sequence represented by SEQ ID NO: 2. Further, the glycoprotein of the present invention includes a variant of SEQ ID NO: 1 within the scope of the present invention. Specifically, the gene may include a base sequence having a sequence homology of 70% or more, more preferably 80%, or most preferably 90% or more with a base sequence of SEQ ID No. 1.

As used herein, "vaccine" is a biological preparation containing an antigen that causes an immune response in an organism, and refers to an immunogen that induces immunity in an organism by injection or oral administration into a human or animal for prevention of an infectious disease. The animal is a human or non-human animal, and the non-human animal refers to a pig, a cow, a horse, a dog, a goat, sheep, and the like, but is not limited thereto.

As used herein, the "expression vector" refers to a vector capable of expressing a peptide or protein encoded by a foreign nucleic acid inserted in the vector, preferably a vector prepared so as to express a target antigen to which a porcine Fc fragment is fused. The "vector" refers to any medium for the introduction and/or transfer of a base into a host cell in vitro, ex vivo, or in vivo, and may be a replicon to which another DNA fragment may be bound to bring about the replication of the bound fragment, and the "replicon" refers to any genetic unit (for example, a plasmid, a phage, a cosmid, a chromosome, a virus, and the like) that functions as an autonomous unit of DNA replication in vivo, that is, one which is capable of replication under its own control. The recombinant expression vector of the present invention may include, preferably, a promoter that is a transcription initiation factor to which RNA polymerase binds, any operator sequence for regulating transcription, a sequence encoding a suitable mRNA ribosome binding site, a sequence regulating termination of transcription and translation, a terminator, and the like, more preferably, may further include a 5' UTR site gene of M17 for increasing the synthesis amount of a protein, a BiP gene for transferring a target protein to the endoplasmic reticulum, an HDEL gene for minimizing the degradation of a protein such that the protein may be stably maintained in the endoplasmic reticulum, and the like, and even more preferably, may further include a selection marker gene such as a tag gene for easily isolating a recombinant protein and an antibiotic resistance gene for selecting a transgenic organism, and the like.

The tag gene may include, for example, an Avi tag, a Calmodulin tag, a polyglutamate tag, an E tag, a FLAG tag, a HA tag, a His tag, a Myc tag, an S tag, a SBP tag, an IgG-Fc tag, a CTB tag, a Softag 1 tag, a Softag 3 tag, a Strep tag, a TC tag, a V5 tag, a VSV tag, an Xpress tag, and the like, the selection marker gene may include, for example, herbicide resistance genes such as glyphosate or phosphinothricin, antibiotic resistance genes such as kanamycin, G418, bleomycin, hygromycin, and chloramphenicol, aadA genes, and the like, the promoter may include, for example, an Emu promoter, a Mannopine synthase (MAS) promoter, a histone promoter, a Clp promoter, a cauliflower-mosaic-virus-derived 35S promoter, a cauliflower-mosaic-virus-derived 19S RNA promoter, an actin protein promoter of a plant, a ubiquitin protein promoter, a cytomegalovirus (CMV) promoter, a simian virus 40 (SV40) promoter, a respiratory syncytial virus (RSV) promoter, an elongation factor-1 alpha (EF-1a) promoter, and the like, representative examples of the terminator include a nopaline synthase (NOS) terminator, a rice amylase A terminator, a phaseolin terminator, a terminator of an octopine gene of *Agrobacterium tumefaciens*, a rmB1/B2 terminator of *E. coli*, and the like, but the examples are only illustrative and are not limited thereto.

As used herein, the "transformation" collectively refers to changes in genetic properties of a living organism by injected DNA, the "transgenic organism" is an organism prepared by injecting an external gene by a molecular genetic method, preferably, an organism transformed by a recombinant expression vector of the present invention, and the organism is not limited as long as it is a living organism such as a microorganism, a eukaryotic cell, an insect, an animal, and a plant, and is preferably *Escherichia coli. Salmonella, Bacillus*, yeast, an animal cell, a mouse, a rat, a dog, a monkey, a pig, a horse, a cow, *Agrobacterium tumefaciens*, a plant, and the like, but is not limited thereto. The transgenic organism may be prepared by a method such as transformation, transfection, *Agrobacterium*-mediated transformation, particle gun bombardment, sonication, electroporation, and polyethylene glycol (PEG)-mediated transformation, but there is no limitation as long as it is a method capable of injecting the vector of the present invention.

As used herein, the "solubility" refers to the degree to which a target protein or peptide can be dissolved in a solvent suitable for administration to the human body. Specifically, the solubility may indicate the degree of solute saturation in a given solvent at a specific temperature. The solubility may be measured by determining the saturation concentration of the solute, and for example, an excessive amount of solute is added to a solvent, the resulting mixture is stirred and filtered, and then the concentration may be measured using a UV spectrophotometer, HPLC, or the like, but the method for measuring the solubility is not limited thereto, and high solubility is advantageous in the isolation and purification of a recombinant protein, and has an advantage in that aggregation of the recombinant protein is inhibited, and thus physiological activity or pharmacological activity of the recombinant protein is maintained.

As used herein, the "prevention" refers to all actions that suppress rabies or delay the onset of rabies by administering the recombinant rabies virus glycoprotein according to the present invention.

As used herein, the "individual" refers to a subject to which the recombinant rabies virus glycoprotein of the present invention may be administered, and the subject is not limited.

The "vaccine composition" of the present invention may be used by being formulated in the form of an oral formulation such as powder, granules, a tablet, a capsule, a suspension, an emulsion, a syrup, and an aerosol, and a sterile injection solution, according to a typical method. When the composition is prepared, the composition may be prepared using a commonly used diluent or excipient, such as a filler, an extender, a binder, a wetting agent, a disintegrant, and a surfactant. A solid formulation for oral formulation includes a tablet, a pill, powder, granules, and the like, and the solid formulation may be prepared by mixing at least one excipient, for example, starch, calcium carbonate, sucrose or lactose, gelatin, and the like with a lecithin-like emulsifier. Further, in addition to simple excipients, lubricants such as magnesium stearate and talc may also be used. As a liquid formulation for oral administration, a suspension, a liquid for internal use, an emulsion, a syrup, and the like may be used, and in addition to water and liquid paraffin which are simple commonly used diluents, various excipients, for example, a wetting agent, a sweetener, an aromatic, a preservative, and the like may be included. Examples of a formulation for parenteral administration include an aqueous sterile solution, a non-aqueous solvent, a suspension, an emulsion, and a freeze-dried preparation. As the non-aqueous solvent and the suspension, it is possible to use propylene glycol, polyethylene glycol, a vegetable oil such as olive oil, an injectable ester such as ethyl oleate, and the like. Furthermore, an "immune antigen adjuvant" conventionally known may be further included. The adjuvant may be used without limitation as long as it is known in the art, but for example, immunogenicity may be enhanced by further including Freund's Complete Adjuvant or Incomplete Adjuvant.

The vaccine composition or pharmaceutical composition of the present invention may be used by being formulated in the form of an oral formulation such as powder, granules, a tablet, a capsule, a suspension, an emulsion, a syrup, and an aerosol, and an external preparation, a suppository, or a sterile injection solution, according to a typical method.

The route of administration of the vaccine composition according to the present invention includes, but is not limited to, oral, intravenous, intramuscular, intraarterial, intramedullary, intrathecal, intracardiac, transdermal, subcutaneous, intraperitoneal, intranasal, intestinal, topical, sublingual or rectal routes. Oral or parenteral administration is preferred. As used herein, the term "parenteral" includes subcutaneous, intradermal, intravenous, intramuscular, intraarticular, intrasynovial, intrasternal, intrathecal, intralesional and intracranial injection or infusion techniques. The vaccine composition of the present invention may also be administered in the form of a suppository for rectal administration.

The dose of the vaccine composition or pharmaceutical composition according to the present invention is selected in consideration of the age, body weight, sex, physical condition and the like of an individual. The amount required to induce an immunoprotective response in an individual without particular side effects may vary depending on the recombinant protein used as an immunogen and the presence of a random excipient. In general, each dose contains 0.1 to 1000 μg, preferably 0.1 to 100 μg of a protein per ml of a sterile solution of the recombinant protein of the present invention.

In the case of the vaccine composition, an initial dose followed by optionally repeated antigenic stimulation may be performed, if necessary.

As used herein, the "adjuvant" generally refers to any material that increases the body fluid and/or cell-mediated immune response to an antigen.

The "feed composition" of the present invention refers to feed including recombinant rabies virus glycoprotein of the present invention, examples of the feed include byproducts such as pork, beef, and chicken, corn, rice, general rice straw, wild grass, grass, silage, hay, mountain wild grass, and the like, but are not limited thereto, and there is no limitation as long as it is used for raising livestock and pet. Examples of a method for adding the recombinant rabies virus glycoprotein of the present invention to feed include a method such as mechanical mixing, adsorption, and occlusion, but are not limited thereto.

Hereinafter, preferred Examples for helping the understanding of the present invention will be suggested. However, the following Examples are provided for easier understanding of the present invention, and the contents of the present invention are not limited by the following Examples.

EXAMPLES

Example 1: Preparation of Vector for Expressing Recombinant Rabies Virus Elycoprotein To prepare an expression vector for expressing a recombinant rabies virus glycoprotein (RVGe) in a plant, as a result of conducting a study to optimize the expression of the protein in the plant body after securing the publically available gene sequences of the rabies virus glycoprotein, a polynucleotide encoding a rabies virus glycoprotein of SEQ ID NO: 1 was obtained. Furthermore, a vector for expressing a recombinant rabies virus glycoprotein was constructed by cloning a polynucleotide (SEQ ID NO: 3) encoding a chaperone binding protein (BiP), a polynucleotide (SEQ ID NO: 1) encoding a rabies virus glycoprotein, a polynucleotide (SEQ ID NO: 4) encoding 6 consecutive histidines, and a polynucleotide (SEQ ID NO: 5) encoding a His-Asp-Glu-Leu (HDEL) peptide in this order between a CaMV 35S promoter gene of a pCAMBIA1300 vector and a NOS terminator.

Example 2: Confirmation of Expression of Recombinant Rabies Virus Glycoprotein

To confirm the expression of a recombinant protein of the vector constructed in the same manner as in Example 1, a transient expression experiment in which transformed *Agrobacterium tumefaciens* was inoculated into the leaves of *Nicotiana benthamiana* was performed. More specifically, an *Agrobacterium* LBA4404 was transformed with a vector for expressing a recombinant rabies virus glycoprotein using electroporation. The transformed *Agrobacterium* was inoculated into 5 ml of a YEP liquid medium (10 g of yeast extract, 10 g of peptone, 5 g of NaCl, 50 mg/l kanamycin, and 25 mg/l rifampicin), and then cultured with shaking under a condition of 28° C. for 16 hours. Then, 1 ml of a culture solution was inoculated into 50 ml of a new YEP medium, the bacteria were again cultured with shaking under a condition of 28° C. for 6 hours, and then the supernatant was removed by centrifuging 50 ml of the obtained culture solution at 4° C. and 7,000 rpm for 5 minutes. Next, obtained bacterial cells were suspended in an infiltration buffer (10 mM MES (pH 5.7), 10 mM $MgCl_2$, and 200 μM acetosyringone) such that $OD_{600\ nm}$=1.0, and Agrobacteria-infiltration was performed by a method of injecting the suspended Agrobacteria into the backside of the leaves of *Nicotiana benthamiana* using a syringe from which the needle had been removed.

Figures 1, 2:
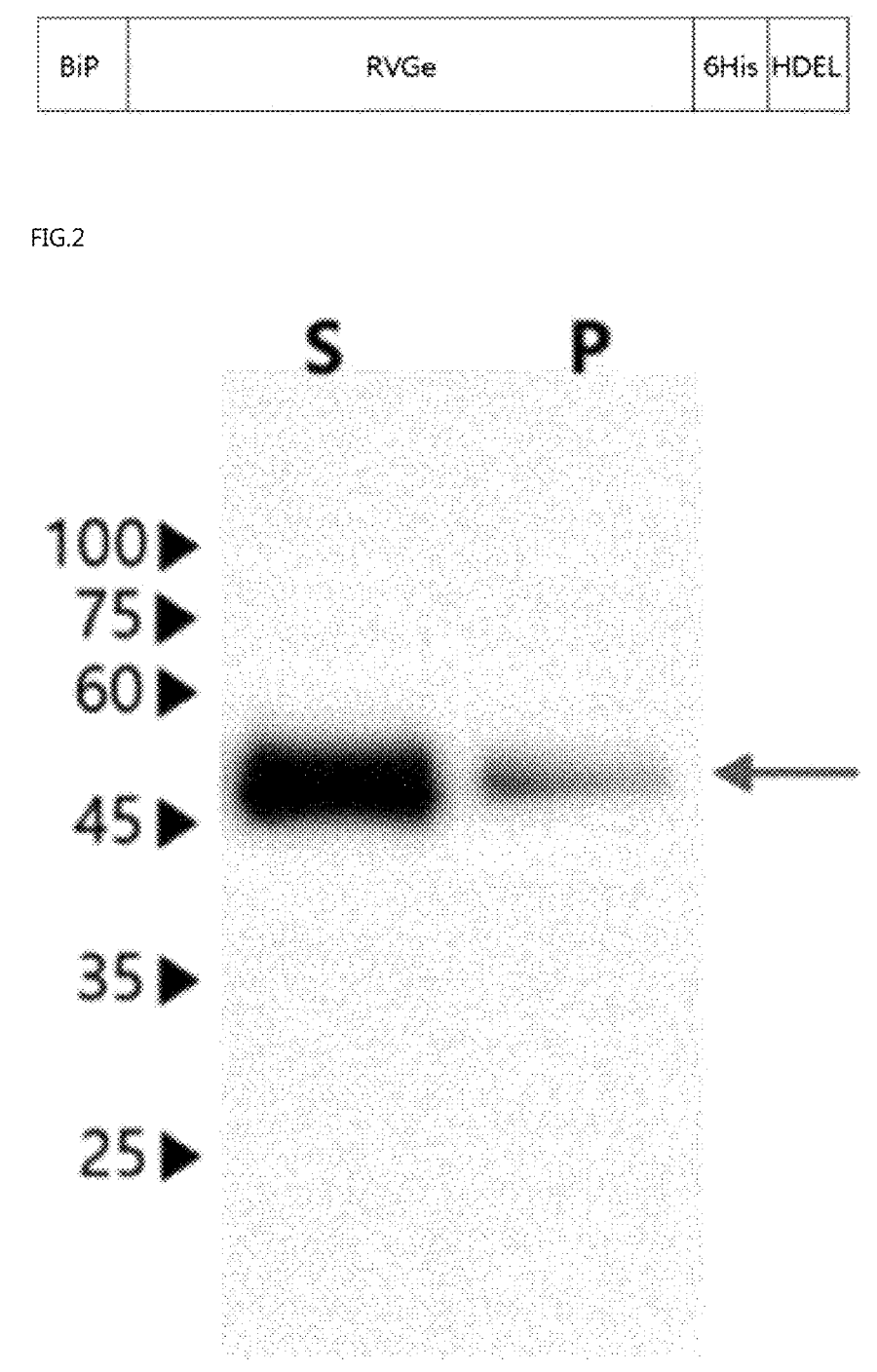

Then, western blotting was performed by extracting a protein from the leaves of *Nicotiana benthamiana* expressing the recombinant rabies virus protein and centrifuging the protein to obtain a recombinant protein (S) included in an aqueous solution fraction and a recombinant protein (P) included in a pellet fraction. During the protein extraction, a 20 mM sodium phosphate (pH 7.3) solution supplemented with 0.1% Triton X-100, 20 mM imidazole (pH 7.5), and 300 mM NaCl was used. For western blotting, after 30 μl of each obtained protein fraction was mixed with an SDS sample buffer, the resulting mixture was heated and electrophoresed on a 10% SDS-PAGE gel to separate proteins by size, and the separated proteins were transferred to a PVDF membrane, then subjected to a blocking step using 5% skim milk, and bound to an antibody reacting with 6 His, and the recombinant rabies virus glycoprotein was confirmed by treating an ECL solution by a method provided by the manufacturer. The results are illustrated in FIG. 2.

As illustrated in FIG. 2, most of the expressed recombinant rabies virus glycoprotein was confirmed in the aqueous fraction (S), and only a small amount of recombinant rabies virus glycoprotein was observed in the pellet fraction (P). Through the results, it could be confirmed that a vector for expressing a recombinant rabies virus glycoprotein of the present invention could effectively express a recombinant rabies virus glycoprotein in a plant body, a recombinant rabies virus glycoprotein prepared using the vector has high solubility, and thus is easy to isolate and purify, and the aggregation of the recombinant protein was suppressed, thereby being effective for maintaining the physiological activity or pharmacological activity of the recombinant protein.

Example 3: Isolation and Purification of Recombinant Rabies Virus Glycoprotein

After 200 ml of a protein extraction solution (50 mM sodium phosphate (pH 8.0), 3(0) mM NaCl, 20 mM imidazole, 0.1% Triton X-100, and a IX protease inhibitor) was added to 40 g of *Nicotiana benthamiana* obtained in the same manner as in Example 2 and a tissue was crushed by a blender, a protein extract was obtained by centrifugation at 4° C. and 13,000 rpm for 20 minutes. Then, in order to isolate and purify the recombinant rabies virus glycoprotein from the protein extract, affinity chromatography was performed using a column packed with a Ni-NTA agarose resin. More specifically, the column was packed with 5 ml of the resin and then equilibrated using 50 ml of a washing buffer (50 mM sodium phosphate (pH 8.0), 300 mM NaCl, and 20 mM imidazole). A protein extract was injected into the equilibrated column, unbound proteins were removed using 100 ml of the washing buffer, and then the recombinant rabies virus glycoprotein was eluted using an elution buffer (50 mM sodium phosphate (pH 8.0), 300 mM NaCl, and 300 mM imidazole). Then, the eluted solution was replaced with phosphate buffered saline (PBS) using a filter having a size of 30 kD, and a recombinant rabies virus glycoprotein was obtained by concentrating the protein. The obtained protein was confirmed by protein electrophoresis (SDS-PAGE) and Coomassie staining. The results are illustrated in FIG. 3.

As illustrated in FIG. 3, it was confirmed that the recombinant rabies virus glycoprotein having a size of about 51 Kd was purified.

Example 4: Confirmation Whether Recombinant Rabies Virus Glycoprotein is Glycosylated In order to confirm whether the recombinant rabies virus glycoprotein obtained in the same manner as in Example 3 was glycosylated, an endo H glycosidase N-glycosylation removal analysis was performed. More specifically, after a 10× denaturation buffer (5% SDS and 0.4 M DTT) was added to 1 μg of the recombinant rabies virus glycoprotein, the resulting mixture was heated at 100° C., and a sodium citrate buffer (pH 5.5) was added such that the final concentration of the recombinant protein was 50 mM. Then, 50 U of endo H glycosidase was added thereto, and the resulting mixture was allowed to react at 37° C. for 1 hour. An experiment was conducted after adding the same amount of distilled water instead of Endo H glycosidase as a control. After the reaction was completed, a change in molecular weight according to the removal of N-glycosylation of the recombinant rabies virus glycoprotein was confirmed by performing western blotting in the same manner as in Example 2. The results are illustrated in FIG. 4.

Figure 4:
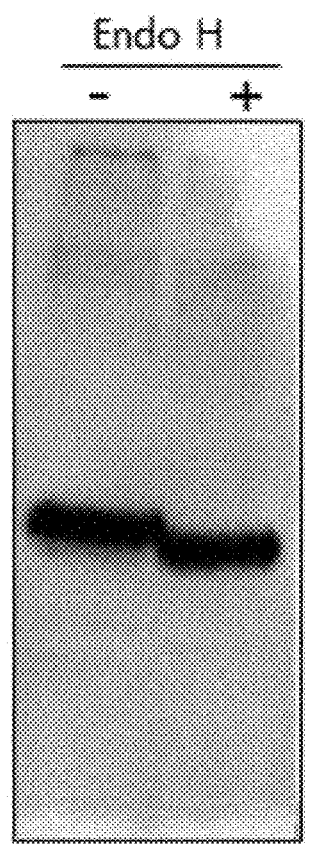
FIG. 4 is a view illustrating the results of confirming whether a recombinant rabies virus glycoprotein according to an exemplary embodiment of the present invention is glycosylated.

As illustrated in FIG. 4, it was confirmed that the molecular weight of recombinant rabies virus glycoprotein was reduced by endo H glycosidase, and through this, it could be confirmed that the recombinant rabies virus glycoprotein obtained using the plant body was normally N-glycosylated.

Example 5. Experiment of Confirming Immunogenicity of Recombinant Rabies Virus Glycoprotein To confirm whether the recombinant rabies virus glycoprotein obtained in the same manner as in Example 3 had immunogenicity by inducing an antibody in vivo as an antigen, an experiment was performed using 6-week old male C57BU6J mice. More specifically, 1 μg of the recombinant rabies virus glycoprotein was administered to experimental group mice (6 to 8-week old), and phosphate buffered saline (PBS) was administered to negative control mice. When the recombinant rabies virus glycoprotein was administered, the same amount of Freund's adjuvant was mixed and administered, a complete adjuvant was primarily administered, and an incomplete adjuvant was secondarily administered. Two weeks after the recombinant rabies virus glycoprotein was administered twice, blood was collected and it was confirmed using an ELISA plate coated with the recombinant rabies virus glycoprotein whether a specific antibody against the administered antigen was generated. An experiment was performed using 4 animals of a negative control (CT) and 5 animals of an experimental group (RVGe), and the results are illustrated in FIG. 5.

As illustrated in FIG. 5, no reactivity was observed in a serum sample (pre) before administration of the recombinant rabies virus glycoprotein and a serum sample (post) after administration of the phosphate buffered saline to the negative control, but it was confirmed that the serum sample after administration of the recombinant rabies virus glycoprotein showed high reactivity. Through the results, it could be confirmed that the recombinant rabies virus glycoprotein of the present invention acted as an antigen and could effectively generate an antibody.

Example 6. Experiment of Confirming Virus Neutralizing Ability of Recombinant Rabies Virus Glycoprotein Using a serum obtained in the same manner as in Example 5, it was confirmed whether an antibody formed by the administration of the rabies virus glycoprotein of the present invention had a rabies virus neutralizing ability. More specifically, 100 μl of a DMEM medium was aliquoted into 4 wells per sample in a 96-well plate, and then 50 μl of serum to be diluted was added to each of the first wells. Then, a 3-fold serial dilution was performed using the remaining three wells in which the medium was aliquoted. 50 μl each of a standard fixed strain virus (CVS11) diluted to a concentration of 100 tissue culture infectious dose $(TCID)_{50}/\mu l$ was added to the last well in which serum dilution was completed, the resulting mixture was allowed to react at 37° C. for 1 hour, and then 50 μl of BHKT7 cells diluted to a concentration of $4\times10^5$ cells/mi using a DMEM medium supplemented with 10% fetal bovine serum (FBS) was inoculated into each well, cultured at 37° C. for 48 hours, and contaminated with viruses. Then, in order to observe the infected cells under a fluorescence microscope, the culture solution was removed, the cells were fixed using 80% acetone, and then fluorescent staining was performed using a rabies-specific antibody to which fluorescence was bound. A sample for confirming the neutralizing ability was prepared by using an World Organization for Animal Health (OIE) standard dog serum diluted to a concentration of 0.5 International Units (IU)/ml as a standard positive serum, using a negative control serum as an antibody negative serum, and inactivating other experimental sera. For the antibody titer of each sample, after a fluorescence value of a fluorescence image obtained using a fluorescence microscope using an ImageJ program, the antibody titer of each sample was calculated using the standard positive serum results. The neutralizing antibody titer was determined to be positive when it was 0.5 IU/ml or higher and negative when it was less than 0.5 IU/ml. The results are shown in Table 1.

TABLE 1

| Antigen | Individual number | Neutralizing antibody titer |
|---------|-------------------|----------------------------|
| RVGe    | 1                 | 4.56 IU/ml                 |
|         | 2                 | 1.51 IU/ml                 |
|         | 3                 | 13.77 IU/ml                |
|         | 4                 | 0.87 IU/ml                 |
|         | 5                 | 23.93 IU/ml                |
|         | Negative          | <0.5 IU/ml                 |

As shown in Table 1, it was confirmed that all the individuals in the experimental group to which the recombinant rabies virus glycoprotein of the present invention was administered twice showed a high titer of virus neutralizing antibody.

Through the results, it could be confirmed that the recombinant rabies virus glycoprotein of the present invention is not only effectively expressed in a plant body, but also has high solubility, and thus is easy to isolate and purify, and the protein activity is also stable. Furthermore, it could be confirmed that the recombinant rabies virus glycoprotein of the present invention shows high immunogenicity and virus neutralizing activity, and thus can be used as a novel rabies vaccine composition.

Hereinafter, the preparation examples of the pharmaceutical composition and feed composition of the present inven-

Preparation Example 1. Preparation of Pharmaceutical Composition 1.1. Preparation of Powder
  Recombinant rabies virus glycoprotein 20 mg
  Lactose 100 mg
  Talc 10 mg
  A powder is prepared by mixing the ingredients and filling an airtight pack with the ingredients.

1.2. Preparation of Tablets
  Recombinant rabies virus glycoprotein 10 mg
  Corn starch 100 mg
  Lactose 100 mg
  Magnesium stearate 2 mg
  After the ingredients are mixed, tablets are prepared by tableting the mixture according to a typical tablet preparation method.

1.3. Preparation of Capsules
  Recombinant rabies virus glycoprotein 10 mg
  Crystalline cellulose 3 mg
  Lactose 14.8 mg
  Magnesium stearate 0.2 mg
  Capsules are prepared by mixing the ingredients according to a typical capsule preparation method and filling gelatin capsules with the mixture.

1.4. Preparation of Injection
  Recombinant rabies virus glycoprotein 10 mg
  Mannitol 180 mg
  Sterile distilled water for injection 2,974 mg
  $Na_2HPO_4 2H_2O$ 26 mg
  According to the typical method for preparing an injection, an injection is prepared in a content of the ingredients per 1 ampoule (2 ml).

1.5. Preparation of Liquid
  Recombinant rabies virus glycoprotein 20 mg
  Isomerized sugar 10 g
  Mannitol 5 g
  Purified water appropriate amount
  According to a typical method for preparing a liquid, each ingredient is added to purified water and dissolved, an appropriate amount of lemon flavor is added, and then the ingredients are mixed, and then purified water is added thereto to adjust the total volume to 100 ml, and then a liquid is prepared by filling a brown bottle with the mixture and sterilizing the brown bottle.

Preparation Example 2. Preparation of Feed Composition

Recombinant rabies virus glycoprotein 100 mg
  Vitamin E 0.7 mg
  L-carnitine 0.7 mg
  According to a typical method for preparing feed, feed is prepared by mixing the ingredients.

The above-described description of the present invention is provided for illustrative purposes, and a person skilled in the art to which the present invention pertains will understand that the present invention can be easily modified into other specific forms without changing the technical spirit or essential features of the present invention. Therefore, it should be understood that the above-described embodiments are only illustrative in all aspects and not restrictive.

INDUSTRIAL APPLICABILITY

The present invention relates to a rabies virus glycoprotein including an amino acid sequence represented by SEQ ID NO: 2, an expression vector for producing the glycoprotein, a transgenic organism transformed with the expression vector, a vaccine composition for preventing rabies, including the glycoprotein as an active ingredient, and the like, and the rabies virus glycoprotein of the present invention is not only effectively expressed in a plant, but also has high solubility, and thus is easy to isolate and purify, thereby being expected to enable the rabies virus glycoprotein to be mass-produced at low cost.

The invention claimed is:

1. A vector for expressing a rabies virus glycoprotein in a plant, comprising a polynucleotide encoding a BiP (chaperone binding protein), a polynucleotide set forth in SEO ID NO:1 encoding a rabies virus glycoprotein, and a polynucleotide encoding a His-Asp-Glu-Leu (HDEL) peptide.

2. A transgenic organism transformed with the vector of claim 1.

3. The vector of claim 1, wherein the polynucleotide encoding the BiP comprises the polynucleotide sequence set forth in SEQ ID NO:3.

4. The vector of claim 1, further comprising a polynucleotide encoding 6 consecutive histidines.

5. The vector of claim 4, wherein the polynucleotide encoding the BiP, the polynucleotide encoding the rabies virus glycoprotein, the polynucleotide encoding 6 consecutive histidines, and the polynucleotide encoding the His-Asp-Glu-Leu (HDEL) peptide are sequentially linked.

6. The transgenic organism of claim 2, wherein the organism is *Agrobaclerium tumefaciens* or a plant.

\* \* \* \* \*

SEQUENCE LISTING

```
<160> NUMBER OF SEQ ID NOS: 5

<210> SEQ ID NO 1
<211> LENGTH: 1314
<212> TYPE: DNA
<213> ORGANISM: Artificial Sequence
<220> FEATURE:
<223> OTHER INFORMATION: DNA sequence of RVGe

<400> SEQUENCE: 1
aaattcccca tctacacgat accggataaa cttggtcctt ggtctccaat tgatattcat      60
catctcagct gtccaaataa tctggttgtc gaggatgaag ggtgtaccaa cttgtcaggt     120
ttttcctata tggaacttaa agtgggatac atttcggcca taaaagtgaa cggctttacg     180
tgcacaggtg tggtgacaga ggcggaaacg tatactaatt tcgttgggta tgtgactact     240
accttcaaaa gaaagcattt tcgcccgaca ccggacgcct gtcgggcggc ttataattgg     300
aaaatggccg gtgacccgcg ttatgaggaa tctctgcata atccgtaccc agattatcac     360
tggttacgaa ctgtgaagac cacgaaagaa agtctggtta tcatctcccc aagtgtagcg     420
gacctggacc catatgataa atctcttcac agccgcgtct ttcctaacgg aaagtgcagc     480
```

-continued

```
ggcataacga tttcttctac ctactgccct accaaccatg attacacaat ctggctgccc    540
gagaatccgc gcctgggcac atcttgcgat atttttacca acagtagagg taaacgggca    600
tctaaaggga gcaagacctg tgggtttgtt gatgaacgtg gtctgtacaa atcattgaaa    660
ggagcatgca aattaaaatt atgcggggtc cttgggcttc gtctgatgga tggtacgtgg    720
gtagcgatgc aggcgtcgga cgaaaccaaa tggtgccctc cagatcagct ggtaaatcta    780
cacgactttc gcagtgacga gatagaacat ctcgttgtgg aggaacttgt caaaaagcga    840
gaagaatgtt tagacgcatt agagtccatc atgactacta agtcagtgag tttccggcgt    900
ctgagccact tgcgtaaatt ggtccccggc tttggaaaag catacacaat cttcaacaag    960
acattaatgg aagctgacgc tcactataag agtgttcgca cctggaatga aataatcccc   1020
tccaaagggt gtctgcgtgt gggcgggagg tgtcatcctc atgtaaacgg cgtatttttc   1080
aatggcatta tcctgggtcc tgatggccat gttctaatcc cggaaatgca atcaagcctc   1140
cttcagcaac acatggagtt gttggaatcc tcagtcatcc ccctgatgca tccgctggcc   1200
gatccgtcta cagttttcaa agatggcgat gaagcagaga actttgtgga ggttcacctt   1260
ccggatgtac ataaacagat ctcgggagtt gatctgggtc tccctaactg gggg         1314
```

<210> SEQ ID NO 2
<211> LENGTH: 438
<212> TYPE: PRT
<213> ORGANISM: Artificial Sequence
<220> FEATURE:
<223> OTHER INFORMATION: Amino acid sequence of RVGe

<400> SEQUENCE: 2

```
Lys Phe Pro Ile Tyr Thr Ile Pro Asp Lys Leu Gly Pro Trp Ser Pro
1               5                   10                  15

Ile Asp Ile His His Leu Ser Cys Pro Asn Asn Leu Val Val Glu Asp
            20                  25                  30

Glu Gly Cys Thr Asn Leu Ser Gly Phe Ser Tyr Met Glu Leu Lys Val
        35                  40                  45

Gly Tyr Ile Ser Ala Ile Lys Val Asn Gly Phe Thr Cys Thr Gly Val
    50                  55                  60

Val Thr Glu Ala Glu Thr Tyr Thr Asn Phe Val Gly Tyr Val Thr Thr
65                  70                  75                  80

Thr Phe Lys Arg Lys His Phe Arg Pro Thr Pro Asp Ala Cys Arg Ala
                85                  90                  95

Ala Tyr Asn Trp Lys Met Ala Gly Asp Pro Arg Tyr Glu Glu Ser Leu
            100                 105                 110

His Asn Pro Tyr Pro Asp Tyr His Trp Leu Arg Thr Val Lys Thr Thr
        115                 120                 125

Lys Glu Ser Leu Val Ile Ile Ser Pro Ser Val Ala Asp Leu Asp Pro
    130                 135                 140

Tyr Asp Lys Ser Leu His Ser Arg Val Phe Pro Asn Gly Lys Cys Ser
145                 150                 155                 160

Gly Ile Thr Ile Ser Ser Thr Tyr Cys Pro Thr Asn His Asp Tyr Thr
                165                 170                 175

Ile Trp Leu Pro Glu Asn Pro Arg Leu Gly Thr Ser Cys Asp Ile Phe
            180                 185                 190

Thr Asn Ser Arg Gly Lys Arg Ala Ser Lys Gly Ser Lys Thr Cys Gly
        195                 200                 205

Phe Val Asp Glu Arg Gly Leu Tyr Lys Ser Leu Lys Gly Ala Cys Lys
    210                 215                 220
```

```
Leu Lys Leu Cys Gly Val Gly Leu Arg Leu Met Asp Gly Thr Trp
225                 230                 235                 240

Val Ala Met Gln Ala Ser Asp Glu Thr Lys Trp Cys Pro Pro Asp Gln
                245                 250                 255

Leu Val Asn Leu His Asp Phe Arg Ser Asp Glu Ile Glu His Leu Val
            260                 265                 270

Val Glu Glu Leu Val Lys Lys Arg Glu Glu Cys Leu Asp Ala Leu Glu
        275                 280                 285

Ser Ile Met Thr Thr Lys Ser Val Ser Phe Arg Arg Leu Ser His Leu
    290                 295                 300

Arg Lys Leu Val Pro Gly Phe Gly Lys Ala Tyr Thr Ile Phe Asn Lys
305                 310                 315                 320

Thr Leu Met Glu Ala Asp Ala His Tyr Lys Ser Val Arg Thr Trp Asn
                325                 330                 335

Glu Ile Ile Pro Ser Lys Gly Cys Leu Arg Val Gly Gly Arg Cys His
            340                 345                 350

Pro His Val Asn Gly Val Phe Phe Asn Gly Ile Ile Leu Gly Pro Asp
        355                 360                 365

Gly His Val Leu Ile Pro Glu Met Gln Ser Ser Leu Leu Gln Gln His
    370                 375                 380

Met Glu Leu Leu Glu Ser Ser Val Ile Pro Leu Met His Pro Leu Ala
385                 390                 395                 400

Asp Pro Ser Thr Val Phe Lys Asp Gly Asp Glu Ala Glu Asn Phe Val
                405                 410                 415

Glu Val His Leu Pro Asp Val His Lys Gln Ile Ser Gly Val Asp Leu
            420                 425                 430

Gly Leu Pro Asn Trp Gly
            435

<210> SEQ ID NO 3
<211> LENGTH: 273
<212> TYPE: DNA
<213> ORGANISM: Artificial Sequence
<220> FEATURE:
<223> OTHER INFORMATION: DNA sequence of chapherone binding protein

<400> SEQUENCE: 3
atggctcgct cgtttggagc taacagtacc gttgtgttgg cgatcatctt cttcggtgag      60
tgattttccg atcttcttct ccgatttaga tctcctctac attgttgctt aatctcagaa     120
ccttttttcg ttgttcctgg atctgaatgt gtttgtttgc aatttcacga tcttaaaagg     180
ttagatctcg attggtattg acgattggaa tctttacgat ttcaggatgt ttatttgcgt     240
tgtcctctgc aatagaagag gctacgaagt taa                                   273

<210> SEQ ID NO 4
<211> LENGTH: 18
<212> TYPE: DNA
<213> ORGANISM: Artificial Sequence
<220> FEATURE:
<223> OTHER INFORMATION: DNA sequence of 6 His

<400> SEQUENCE: 4
caccaccatc accaccat                                                    18

<210> SEQ ID NO 5
<211> LENGTH: 12
<212> TYPE: DNA
```

```
<213> ORGANISM: Artificial Sequence
<220> FEATURE:
<223> OTHER INFORMATION: DNA sequence of HDEL

<400> SEQUENCE: 5
catgatgagc tc                                                        12
```